US008414507B2

(12) United States Patent
Asada

(10) Patent No.: US 8,414,507 B2
(45) Date of Patent: Apr. 9, 2013

(54) BODY MOTION BALANCE DETECTION DEVICE, BODY MOTION BALANCE DETECTION PROGRAM, BODY MOTION BALANCE DETECTION METHOD, AND BODY MOTION BALANCE DIAGNOSIS METHOD

(75) Inventor: Yuji Asada, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 0 days.

(21) Appl. No.: 13/091,940

(22) Filed: Apr. 21, 2011

(65) Prior Publication Data

US 2011/0196264 A1 Aug. 11, 2011

Related U.S. Application Data

(63) Continuation of application No. PCT/JP2009/005973, filed on Nov. 10, 2009.

(30) Foreign Application Priority Data

Nov. 18, 2008 (JP) .................................. 2008-294572

(51) Int. Cl.
*A61B 5/103* (2006.01)
*A61B 5/117* (2006.01)
(52) U.S. Cl. ...................................................... 600/595
(58) Field of Classification Search .................. 600/300, 600/587–595; 73/65.01–65.09, 489–490, 73/492, 597; 702/144, 160, 176, 182; 324/160
See application file for complete search history.

(56) References Cited

U.S. PATENT DOCUMENTS

| 8,206,325 | B1* | 6/2012 | Najafi et al. | 600/595 |
| 2006/0195050 | A1* | 8/2006 | Alwan et al. | 600/595 |
| 2006/0251334 | A1* | 11/2006 | Oba et al. | 382/275 |

FOREIGN PATENT DOCUMENTS

| JP | A-2001-218754 | 8/2001 |
| JP | A-2007-236779 | 9/2007 |
| JP | A-2008-229266 | 10/2008 |
| JP | A-2008-264114 | 11/2008 |

OTHER PUBLICATIONS

Matsubara et al.; "Gait Analysis Focusing on Gait Balance for Falling Prevention;" *Proceedings of the National Meeting of Information Processing Society of Japan*; Mar. 13, 2008, pp. 4.785-4.786 (with translation).
Ogura et al.; "Identifying the Characteristic Acceleration Patterns by Using Accelerographic Analysis of the Pelvis in Normal Walking;" Rigakuryoho Kagaku; 2005; pp. 171-177; vol. 20, No. 2.
International Search Report dated Feb. 2, 2010 in corresponding International Application No. PCT/JP2009/005973.

(Continued)

*Primary Examiner* — Rene Towa
(74) *Attorney, Agent, or Firm* — Oliff & Berridge PLC

(57) ABSTRACT

A body motion measurement device capable of detecting a body motion balance without installing a pressure sensor is provided. The body motion measurement device includes an acceleration detection unit for detecting a change in acceleration by walking, a calculation unit for detecting a walking balance from the acceleration signal detected by the acceleration detection unit, and a display unit for performing an output based on the detected walking balance. The calculation unit for detecting the walking balance executes step and step of recognizing one step unit of walking from the acceleration signal and acquiring PPodd, PPeven, Todd, and Teven, which are the foot information, and steps of detecting the walking balance based on the foot information.

9 Claims, 7 Drawing Sheets

OTHER PUBLICATIONS

Nov. 20, 2012 Office Action issued in Japanese Patent Application No. 2008-294572 w/translation.

* cited by examiner (A)

[Normal walking]

(B)

[Walking while nursing left foot]

(A)

[Walking with upper half of body tilted to right]

(B)

[Walking with upper half of body tilted to left]

BODY MOTION BALANCE DETECTION DEVICE, BODY MOTION BALANCE DETECTION PROGRAM, BODY MOTION BALANCE DETECTION METHOD, AND BODY MOTION BALANCE DIAGNOSIS METHOD

TECHNICAL FIELD

The present invention relates to a body motion balance detection device, a body motion balance detection program, a body motion balance detection method, and a body motion balance diagnosis method of detecting a body motion balance in exercises such as forward motions including walking and running or in-situ exercises including stepping and thigh-up.

BACKGROUND ART

The balance and symmetry are conventionally known as important elements in evaluating the beauty of a posture. Thus, the evaluation of the balance is considered useful for the beauty of walking and for progress management of rehabilitation.

On the other hand, a walking determination device has been proposed (see patent document 1) for the conventional technique of evaluating the posture at the time of walking. Such a walking determination device measures the foot pressure distribution of a walker by making the walker walk on a pressure sensor installed on the floor to evaluate the beauty of walking and the health degree.

Such a walking determination device, however, cannot be used at a place where the pressure sensor is not installed such as in walking in daily life, and thus lacks in convenience.

Patent Document 1: Japanese Unexamined Patent Publication No. 2001-218754

DISCLOSURE OF THE INVENTION

Problems to be Solved by the Invention

In view of such problems, it is an object of the present invention to provide a body motion balance detection device, a body motion balance detection program, a body motion balance detection method, and a body motion balance diagnosis method capable of detecting the body motion balance by a bias in an exercise for each foot even if the pressure sensor is not installed.

Means for Solving the Problem

The present invention provides a body motion balance detection device including a body motion related signal acquiring means for acquiring a body motion related signal in which a change by the body motion of a living body is detected by being carried around the living body; a body motion balance detection means for detecting a body motion balance from the body motion related signal acquired by the body motion related signal acquiring means; and an output means for performing an output based on the detected body motion balance; wherein the body motion balance detection means is configured to execute a foot information acquiring process of recognizing one step unit from the body motion related signal, and acquiring foot information on each foot separated by foot, and a body motion balance detection process of detecting the body motion balance based on the foot information; and a means for detecting whether walking or not from the body motion related signal is arranged, the detection of the body motion balance by the body motion balance detection means being executed when detected as walking.

The body motion related signal acquiring means can be configured by a means for acquiring the signal related to the body motion such as an acceleration signal acquiring means for acquiring an acceleration signal in which a change in acceleration by the body motion is detected or a means for acquiring a signal in which other changes by the body motion are detected, or a reception means for receiving the body motion related signal acquired by these means by wire or wirelessly. The acceleration signal acquiring means can be configured by an acceleration sensor for detecting the change in acceleration or a reception means for receiving the acceleration signal in which the change in acceleration is detected by wire or wirelessly. The acceleration sensor may be configured by a one-dimensional acceleration sensor for detecting an acceleration in one direction, a two-dimensional acceleration sensor for detecting accelerations in two orthogonal directions, or a three-dimensional acceleration sensor for detecting accelerations in three orthogonal directions.

The body motion balance may be a body motion balance due to the bias in an exercise for each foot in exercises such as forward motions including walking and running, or in situ exercises including stepping and thigh up. Specifically, the body motion balance is the body motion balance of the right foot and the left foot in a living body walking with two legs, or the body motion balance of the right front leg, the left front leg, the right back leg, and the left back leg in a living body walking with four legs.

The output means can be configured by an appropriate means that performs an output such as a display means for performing display, an illumination means for performing lighting or flashing, an audio output means for performing an audio output, a vibration means for performing vibration, a communication means for transmitting information, or the like.

The output by the output means may be an appropriate output such as an output on satisfactory or unsatisfactory of the body motion balance, an output on whether the body motion balance is tilted to left, tilted to right, or normal, an output on whether the step interval of each foot is even or biased, an output on the unsatisfactory level of the body motion balance, or a plurality of the above.

For instance, when displaying on the display means, the output may be made by an appropriate display method such as displaying with patterns, marks, characters, and the like, or displaying by whether or not displaying is carried out only when abnormality is found.

In the output by the illumination means, the output can be made by an appropriate switching of the illumination such as switching between light ON and light OFF, switching between flashing and light OFF, switching the lighting color, and the like when there is abnormality and when there is no abnormality.

In the output by the audio output means, a notification may be made by an appropriate audio such as notifying satisfactory or unsatisfactory, the state, and the like by audio, issuing an alarm sound or notifying abnormality when there is abnormality, and the like.

In the output by the vibration means, the output may be made through an appropriate method such as vibrating only when there is abnormality, differing the vibration amount depending on the extent of abnormality, and the like.

In the output by the communication means, the reception side (information processing terminal that directly or indirectly receives data from the body motion balance detection device) can transmit appropriate data in which satisfactory and unsatisfactory etc. of the body motion balance can be output by the display means, the illumination means, the audio output means, or the vibration means such as outputting satisfactory/unsatisfactory data or outputting numerical value data.

The body motion balance detection device may be a body motion measurement device for measuring the body motion or an appropriate information processing device for acquiring data from the body motion measurement device. The body motion measurement device may be a passometer for counting the number of steps, or an activity amount measurement device for measuring an activity amount. The information processing device may be a portable information processing device such as a portable telephone, a PDA, or a notebook computer, or an installing type information processing device such as a desktop computer or a server computer.

The foot information on each foot separated by foot may be information regarding the respective foot sent out in order or alternately in an exercise such as odd number step and even number step or left foot and right foot in a living body walking with two legs, first to fourth steps or right front foot, left front foot, right back foot, and left back foot or odd number step and even number step in a living body walking with four legs.

According to the present invention, the body motion balance by the bias in an exercise for each foot can be detected even if the pressure sensor is not installed.

The body motion balance in the relationship of the respective foot can be further detected.

In an aspect of the present invention, the foot information acquiring process can be configured to acquire information of an odd number step and information of an even number step by separating the foot information to the odd number step and the even number step; and the body motion balance detection process can be configured to detect the abnormal balance of the body motion balance by comparing the information of the odd number step and the information of the even number step.

In an aspect of the present invention, the body motion balance detection process can be configured to compare an average value of the information of the odd number step and an average number of the information of the even number step.

In an aspect of the present invention, the body motion balance detection means can be configured to execute a continuity determination process of determining whether or not the body motion capable of continuously acquiring the information for every step, which becomes the foot information from the body motion related signal, and execute the foot information acquiring process and the body motion balance detection process if the information is continuously acquired for a predetermined number of steps; and not to execute the detection of the body motion balance if the information is not continuously acquired for a predetermined number of steps.

Therefore, the body motion balance can be detected when continuously exercising, and the accuracy of the body motion balance to be detected can be enhanced.

In an aspect of the present invention, a criterion specification accepting means for allowing specification by a user of the criterion for determining satisfactory and unsatisfactory of the body motion balance is further arranged; wherein the body motion balance detection process can be configured to determine whether or not the foot information satisfies the criterion.

The user may be a person who uses the body motion balance detection device such as an exercising living body itself wearing the body motion balance detection device, or an instructor, a doctor, a care personnel or the like for evaluating or diagnosing the exercise of the exercising living body wearing the body motion balance detection device.

According to such an aspect, the user can define the criterion of the body motion balance by himself/herself. Therefore, the criterion maybe set to be lenient at the beginning and then the criterion may be ultimately set to be harsh, and thus the criterion can be changed in accordance with the progress situation of the exercise training.

In an aspect of the present invention, the body motion related signal can be configured to include at least one of an acceleration signal in a vertical direction of an exercising living body, or an acceleration signal in a horizontal direction of the exercising living body.

The acceleration signal useful for the detection of the body motion balance thus can be acquired.

The present invention may be a body motion measurement device including a portable body motion detection sensor for detecting a change in body motion of a living body by being carried around the living body; a number of steps counting means for counting the number of steps from a body motion related signal detected by the portable body motion detection sensor; a body motion balance detection means for detecting body motion balance from the body motion related signal detected by the portable body motion detection sensor; a display means for performing a number of steps display of the counted number of steps counted by the number of steps counting means and a body motion balance display based on the body motion balance detected by the body motion balance detection means; a storage means for storing at least the counted number of steps; and a power supply means for supplying power to each means, wherein the body motion balance detection means is configured to execute a foot information acquiring process of recognizing one step unit from the body motion related signal, and acquiring foot information on each foot separated by foot, and a body motion balance detection process of detecting the body motion balance based on the foot information; and a means for detecting whether walking or not from the body motion related signal is arranged, the detection of the body motion balance by the body motion balance detection means being executed when detected as walking.

The exercise amount measurement means can be configured by the number of steps counting means for counting the number of steps in walking or running, or an activity amount measurement means for measuring an activity amount in walking, cleaning, and the like.

According to such an aspect, a body motion measurement device capable of detecting the body motion balance by the bias in an exercise for each foot even if the pressure sensor is not installed can be provided.

The present invention may also be a body motion balance detection program for allowing a computer to function as a body motion related signal acquiring means for acquiring a body motion related signal in which a change by the body motion of a living body is detected by being carried around the living body; a means for detecting whether walking or not from the body motion related signal; a body motion balance detection means for detecting a body motion balance from the body motion related signal; and an output means for performing an output based on the detected body motion balance, wherein a foot information acquiring process of recognizing one step unit from the body motion related signal, and acquiring foot information on each foot separated by foot, and a body motion balance detection process of detecting the body motion balance based on the foot information are configured to be executed as the body motion balance detection means;

and the detection of the body motion balance by the body motion balance detection means is configured to be executed when detected as walking.

Therefore, the body motion balance detection program can be installed in an appropriate computer to create a body motion balance detection device.

The present invention may also be a body motion balance detection method including the steps of detecting a body motion balance from a body motion related signal in which a change by the body motion of a living body is detected by being carried around the living body; and performing an output based on the detected body motion balance, wherein the body motion balance detection step is configured to perform a foot information acquiring process of recognizing one step unit from the body motion related signal, and acquiring foot information on each foot separated by foot, and a body motion balance detection process of detecting the body motion balance based on the foot information; and the method further includes a step of detecting whether walking or not from the body motion related signal, the detection of the body motion balance by the body motion balance detection step being executed when detected as walking.

The balance of the body motion thus can be detected.

The present invention may also be a body motion balance diagnosis method including attaching a body motion balance detection device on a median line of an exercising living body, the body motion balance detection device including a body motion related signal acquiring means for acquiring a body motion related signal in which a change by the body motion of the living body is detected; a body motion balance detection means for detecting a body motion balance from the body motion related signal acquired by the body motion related signal acquiring means; and an output means for performing an output based on the detected body motion balance, the body motion balance detection means being configured to execute a foot information acquiring process of recognizing one step unit from the body motion related signal, and acquiring foot information on each foot separated by foot, and a body motion balance detection process of detecting the body motion balance based on the foot information; and a means for detecting whether walking or not from the body motion related signal being arranged, the detection of the body motion balance by the body motion balance detection means being executed when detected as walking; and making a diagnosis of the body motion balance according to the output based on the body motion balance from the output means.

Accordingly, instructors, doctors and the like can diagnose the body motion balance of the exercising living body. Therefore, it can be used to correct the posture at the time of exercise, grasp the recovery of the exercise ability by rehabilitation, and the like.

Effect of the Invention

According to the present invention, the body motion balance by a bias in an exercise for each foot can be detected even if the pressure sensor is not installed.

DESCRIPTION OF SYMBOLS

Figure 1:
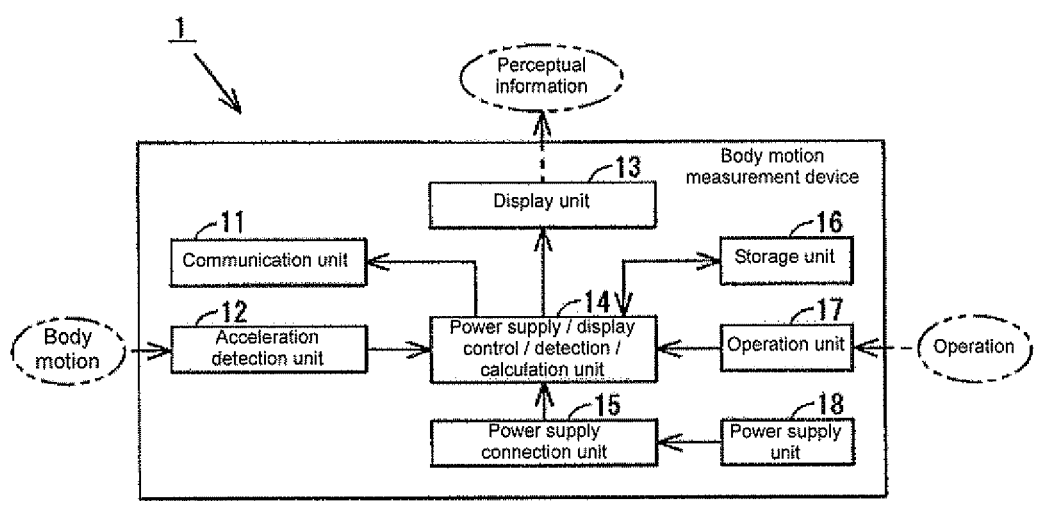
FIG. 1 is a block diagram showing a configuration of a body motion measurement device.

1 body motion measurement device
12 acceleration detection unit
13 display unit
14 calculation unit
16 storage unit
17 operation unit
18 power supply unit

BEST MODE FOR CARRYING OUT THE INVENTION

An example of a body motion measurement device for detecting a walking balance, which is one of body motion balances, will be described below with reference to drawings as one embodiment of the present invention.

FIG. 1 is a block diagram showing a configuration of a body motion measurement device 1.

The body motion measurement device 1 includes a communication unit 11, an acceleration detection unit 12, a display unit 13, a calculation unit 14, a power supply connection unit 15, a storage unit 16, an operation unit 17, and a power supply unit 18, and is formed into a size to such an extent that it fits inside the hand of a normal person so that it can be carried around. Such a body motion measurement device is used as a pedmeter for counting the number of steps, or an activity amount measurement device for measuring an activity amount by chores including cleaning, mopping, and the like.

The communication unit 11 can be configured by an appropriate communication interface such as USB (Universal Serial Bus) for wired connection and Bluetooth (Registered trademark) for wireless communication. The communication with an information processing device such as a personal computer, a portable telephone, or PDA (Personal Digital assistants) thus can be realized.

The acceleration detection unit 12 is a sensor for detecting the acceleration of the vibration generated when a user wearing the body motion measurement device 1 walks, and the like, and transmits a detection signal to the calculation unit 14. The acceleration detection unit 12 can be configured by a one-dimensional acceleration sensor for detecting an acceleration in one direction, a two-dimensional acceleration sensor for detecting accelerations in two orthogonal directions, or a three-dimensional acceleration sensor for detecting accelerations in three orthogonal directions, where the three-dimensional acceleration sensor having great amount of information is the most preferable.

The portable type body motion measurement device 1 is preferably attached on a median line of a walker to correctly detect the walking balance by the acceleration detection unit 12, and is, for example, preferably attached to the buckle of a belt or at the central part on the back side of a belt, and more preferably attached to the buckle of a belt.

A difference between the right foot and the left foot in the fluctuation of the acceleration detected by the acceleration detection unit 12 is thus prevented from creating when walked at a satisfactory balance. In other words, for instance, if the body motion measurement device 1 is attached to the right foot, a strong change in acceleration appears when the right foot is placed on the ground and a change in acceleration when the left foot is placed on the ground becomes small as compared with that when the right foot is placed on the ground, but this can be prevented.

Therefore, if the body motion measurement device 1 is attached on the median line, the advancing direction component, the vertical direction component, and the horizontal direction component of an acceleration signal can be easily taken out by configuring the acceleration detection unit 12 with the three-dimensional acceleration sensor.

The display unit 13 is configured by a display device of liquid crystal and the like, and displays information according to a display control signal from the calculation unit 14. The information to be displayed may be information related to walking such as the number of steps and the walking balance.

The calculation unit 14 is driven by the power received from the power supply unit 18 through the power supply connection unit 15, and receives (detects) the detection signal transmitted from the acceleration detection unit 12 and the operation unit 17 to execute electricity supply (power supply) and operation control (display control) on the communication unit 11, the display unit 13, and the storage unit 16. The calculation unit 14 also executes a process of calculation by referencing walking criterion data and one-step criterion data stored in the storage unit 16 based on the detection signal transmitted from the acceleration detection unit 12.

The storage unit 16 stores the acceleration data, which is the detection signal detected by the acceleration detection unit 12, the one-step criterion data for detecting one step among the detection signal, the body motion balance detection program for detecting the walking balance, and the like.

The operation unit 17 accepts an appropriate operation input such as an input operation of user information including weight and length of stride, an input operation of date and time for setting a clock, a display content switching operation for switching the display content to various types of contents including the number of steps, consumed calories, and walking distance, and a data transmission operation of transmitting data to a different information processing terminal connected to the communication unit 11, and transmits the operation input signal to the calculation unit 14.

The operation unit 17 also accepts an operation input on the criterion (first to fourth balance criterion value) for determining satisfactory and unsatisfactory of the walking balance. The operation input of the criterion can be an appropriate input such as selectively specifying from a plurality of criteria prepared in advance, specifying to change by predetermined stages in a digital manner, or specifying to arbitrary change in an analog manner.

The power supply unit 18 is configured by an appropriate portable power supply such as a chargeable battery or a non-chargeable battery.

Figure 2:
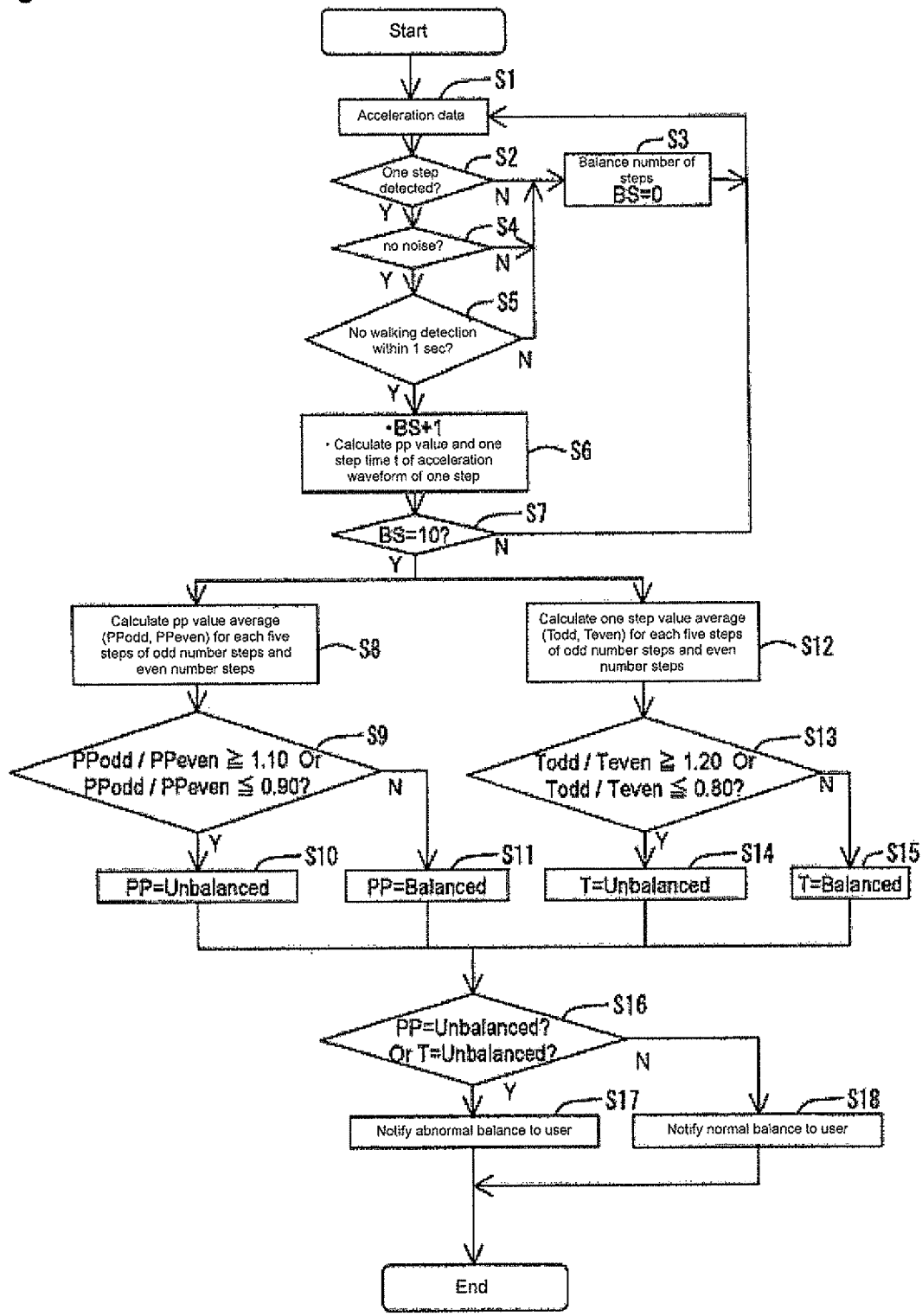
FIG. 2 is a flowchart of the operation executed by a calculation unit of the body motion measurement device.

FIG. 2 is a flowchart of the operation executed by the calculation unit 14 of the body motion measurement device 1 according to the body motion balance detection program.

The calculation unit 14 acquires acceleration data from the acceleration detection unit 12 (step S1), and detects one step from the acceleration data (step S2). The detection of one step may be executed based on appropriate one-step criterion data such as detecting as one step if there is data in which the amplitude from the local maximum value to the local minimum value and the one-step time are in a predetermined time.

If one step is not detected (step S2: No), the calculation unit 14 substitutes value 0 to the balance number of steps BS, which is a variant, and returns to step S1 (step S3).

If one step is detected (step S2: Yes), the calculation unit 14 determines the presence or absence of noise (step S4), and executes step S3 if noise is present (step S4: No).

Figure 3:
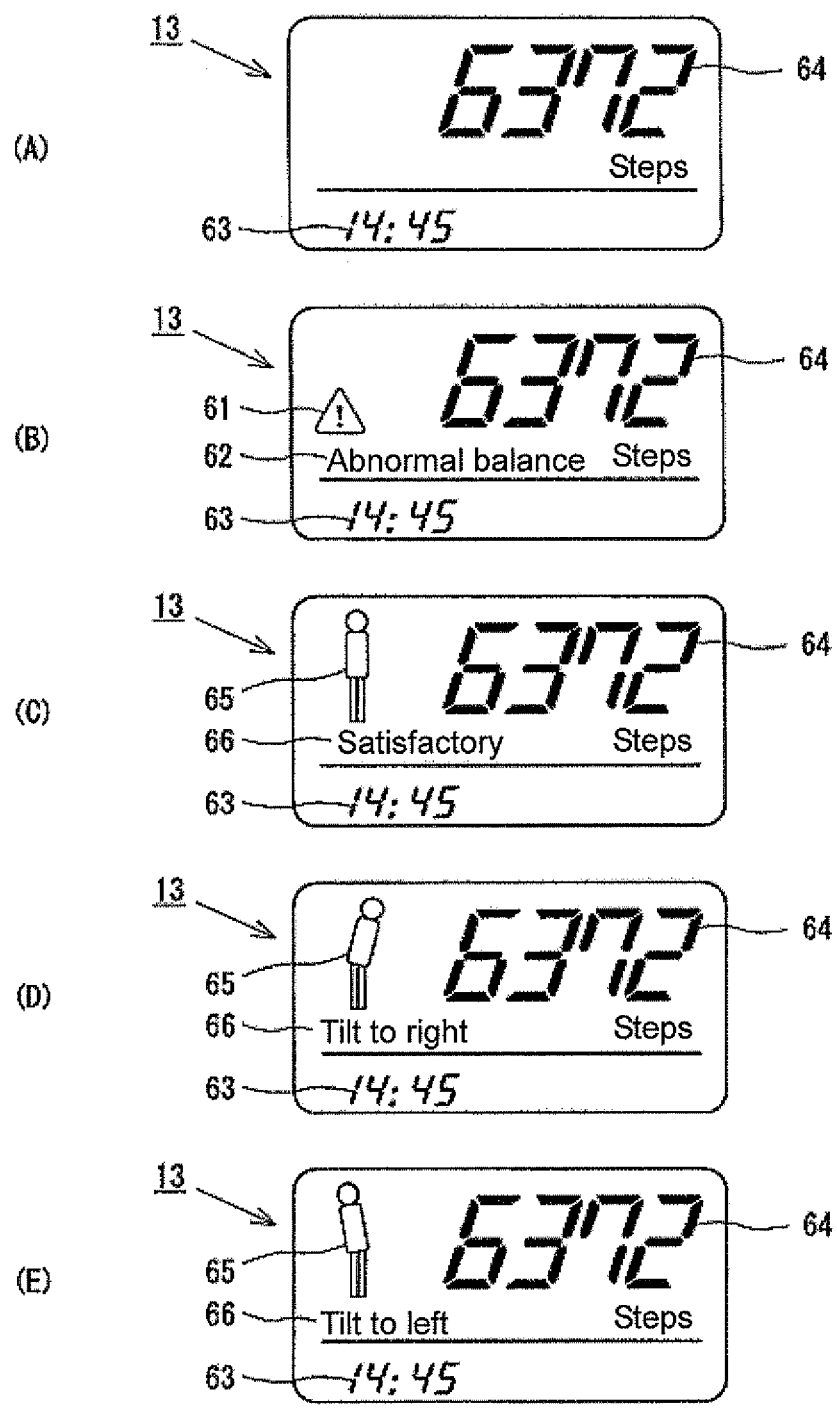
FIGS. 3(A) to 3(E) are views describing a screen image of a display unit.

If noise is absent (step S4: No), the calculation unit 14 determines whether or not no walking detection is within a predetermined time (walking interruption determination time of determining whether or not walking is interrupted, e.g., one second) (step S5), and executes step S3 if the no walking detection exceeds the predetermined time (step S5: No). If noise is not present in step S4, the calculation unit 14 counts the detected one step as the number of step, and displays the counted number of steps on the display unit 13 as shown in the screen image view of FIG. 3(A) and also stores the counted number of steps in the storage unit 16. In the example of FIG. 3(A), the number of steps 64 and the time 63 are displayed on the display unit 13.

If the no walking detection is within the predetermined time (step S5: Yes), the calculation unit 14 adds 1 to the balance number of steps BS and calculates the PP value (amplitude from local maximum value to local minimum value of one step) and the one step time T (time length of the acceleration waveform of one step) in the acceleration waveform of one step (step S6).

The calculation unit 14 repeats steps S1 to S6 described above until the balance number of steps BS becomes a predetermined value (value for determining continuity of a predetermined number of steps, 10 indicating ten steps in the example) (step S7: No).

When the balance number of steps BS reaches the predetermined value (step S7: Yes), the calculation unit 14 executes the walking balance detection process (steps S8 to S11) by the amplitude, and the walking balance detection process (steps S12 to S15) by the one step time.

The calculation unit 14 for performing the walking balance detection process by the amplitude calculates the average value (PPodd) of the PP values of the odd number step of half (five steps in the example) the predetermined value of step S7, and the PP value (PPeven) of the even number step of half the predetermined value of step S7 (step S8).

The calculation unit 14 determines whether or not the even number step PP value (PPodd)/odd number step PP value (PPeven) is greater than or equal to a first balance criterion value (1.10 in the example) or whether or not the even number step PP value (PPodd)/odd number step PP value (PPeven) is smaller than or equal to a second balance criterion value (0.90 in the example) (step S9).

If the even number step PP value (PPodd)/odd number step PP value (PPeven) is greater than or equal to the first balance criterion value or smaller than or equal to the second balance criterion value (step S9: Yes), the calculation unit 14 determines that the walking balance is unsatisfactory and substitutes "Unbalanced", which indicates unsatisfactory walking balance, in the "walking balance PP" that is the variant (step S10).

If the even number step PP value (PPodd)/odd number step PP value (PPeven) is within a range from the first balance criterion value to the second criterion value (step S9: No), the calculation unit 14 determines that the walking balance is satisfactory and substitutes "Balanced", which indicates a satisfactory walking balance, in the "walking balance PP" that is the variant (step S11).

After step S7, the calculation unit 14 for performing the walking balance detection process by the one step time calculates an average value (Todd) of the one step time T of the odd number step of half (five steps in the example) the predetermined value of step S7, and the one step time T (Teven) of the even number step of half the predetermined value of step S7 (step S12).

The information on the odd number step of Todd and PPodd can be made as the information for one foot, the information on the even number step of Teven and PPeven can be made as the information for the other foot, so that the information on one foot and the information on the other foot can be compared.

The calculation unit 14 determines whether or not the one step time T of the even number step (Todd)/one step time T of the odd number step (Teven) is greater than or equal to a third balance criterion value (1.20 in the example) or whether or not the one step time T of the even number step (Todd)/one step time T of the odd number step (Teven) is smaller than or equal to a fourth balance criterion value (0.80 in the example) (step S13).

If the one step time T of the even number step (Todd)/one step time T of the odd number step (Teven) is greater than or equal to the third balance criterion value or smaller than or equal to the fourth balance criterion value (step S13: Yes), the calculation unit 14 determines that the walking balance is unsatisfactory and substitutes "Unbalanced", which indicates an unsatisfactory walking balance, in the "walking balance T" that is the variant (step S14).

If the one step time T of the even number step (Todd)/one step time T of the odd number step (Teven) is within a range from the third balance criterion value to the fourth criterion value (step S13: No), the calculation unit 14 determines that the walking balance is satisfactory and substitutes "Balanced", which indicates a satisfactory walking balance, in the "walking balance T" that is the variant (step S15).

The calculation unit 14 confirms the values of the walking balance PP and the walking balance T, and notifies balance abnormality to the user (step S17) if "Unbalanced" is substituted to either one (step S16: Yes). Various methods can be adopted for a method of notifying the user in this case. For instance, a warning mark 61 or a balance abnormality display 62 indicating balance abnormality may be displayed on the display unit 13, as shown in FIG. 3(B), a picture 65 in which a person is tilted to the right or the left, or a state description character 66 indicating "satisfactory", "tilt to right", or "tilt to left" may be displayed on the display unit 13 as shown in FIG. 3(D) and FIG. 3(E), a separately arranged LED and the like may emit light or flash in red etc., an audio guidance may be made with a separately arranged audio output device, a separately arranged vibration device (vibration device) may be vibrated, or a plurality of the above may be carried out.

When displaying tilt to the right or tilt to the left, the user selects a special mode such as a tilt determination mode, and then specifies or selects whether the first step is the left foot or the right foot in the special mode to carry out the measurement. The calculation unit 14 can then correspond the even number step PP value (PPodd) and the odd number step PP value (PPeven) to the right foot and the left foot, respectively, and whether the tilt to the right or the tilt to the left can be determined from the comparison of the even number step PP value (PPodd) and the odd number step PP value (PPeven), so that the tilt direction can be output as shown in FIG. 3(D) and FIG. 3(E).

The notification on the balance abnormality is preferably executed in real time or at a timing as close as possible to real time during walking. In this case, the user who is walking can know about the balance abnormality without looking at the body motion measurement device 1 if notified by audio or vibration. Thus, the user can correct to balanced walking in situ when notified of the balance abnormality, and can recognize that the walking has been corrected when the notification on the balance abnormality is no longer made.

If "Unbalanced" is not substituted to both the walking balance PP and the walking balance T (step S16: No), the calculation unit 14 notifies a normal balance to the user (step S18).

Various methods can be adopted for a method of notifying the user in this case. For instance, as shown in FIG. 3(C), a "satisfactory" state description character 66 indicating a normal balance may be displayed on the display unit 13, a picture 65 in which a person is standing straight, or walking may be displayed on the display unit 13, a separately arranged LED and the like may emit light or flash in blue etc., a separately arranged vibration device (vibration device) may be vibrated, or a plurality of the above may be carried out. In the case of the normal balance, it can also be configured that a notification may not be made to the user. In such a case, a notification is made only in the case of the balance abnormality, so that the trouble of making the user confirm satisfactory and unsatisfactory of the balance on a constant basis can be omitted.

With the above configuration and operation, satisfactory and unsatisfactory of the walking balance can be detected and output. In particular, detection can be made separately for the odd number step and the even number step, so that the left and right balances or the balance in the horizontal direction of the user being attached at the time of walking can be detected.

Figure 4:
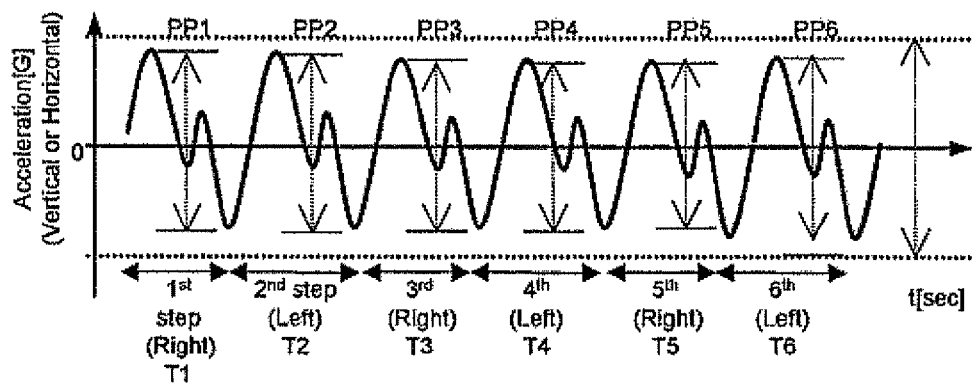
FIGS. 4(A) and 4(B) are views describing an output waveform of an acceleration detection unit at the time of walking.
Figure 4:
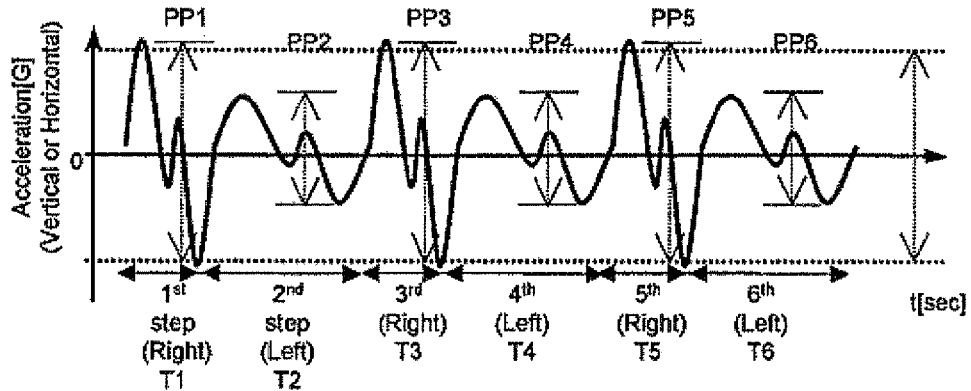
Figure 5:
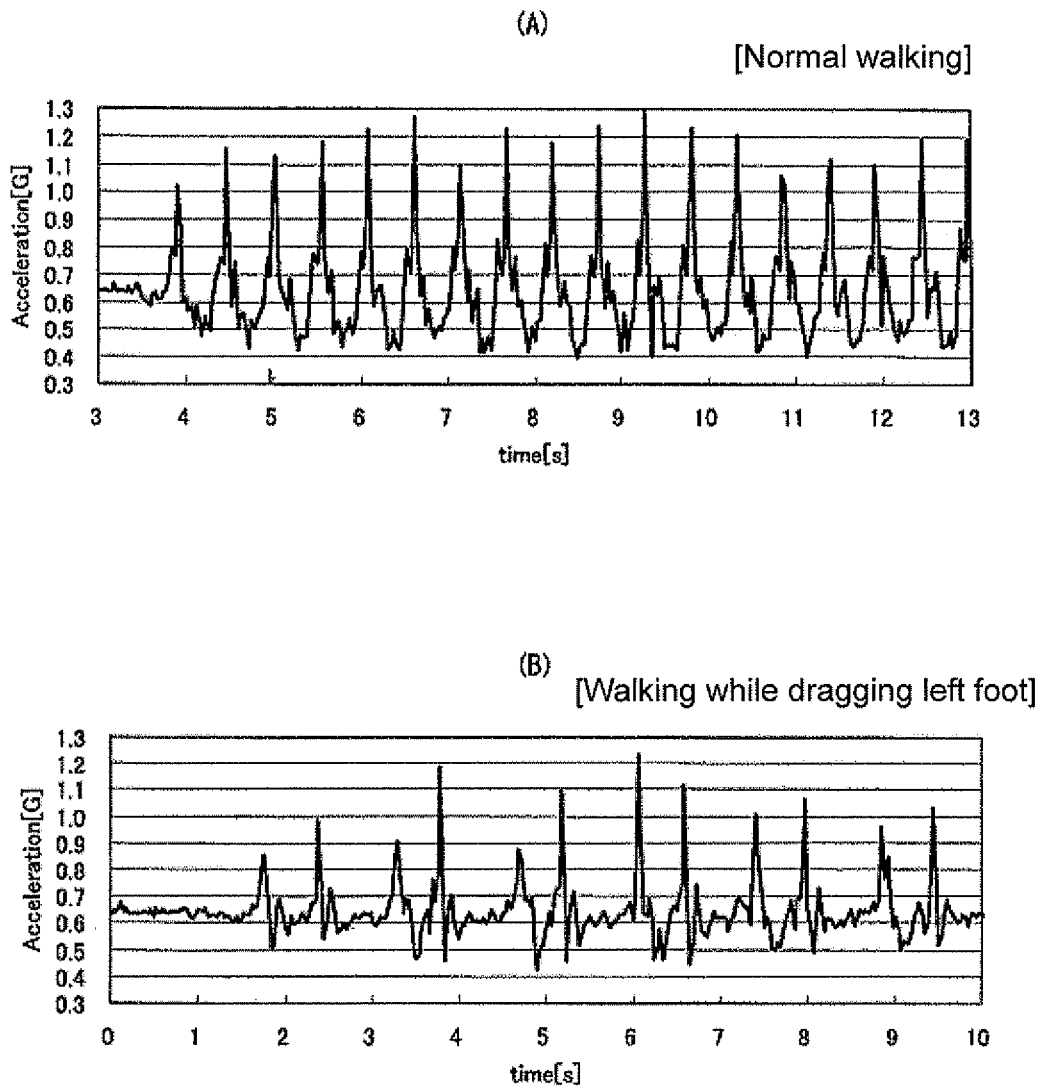
FIGS. 5(A) and 5(B) are views describing an output waveform of an acceleration detection unit at the time of walking.

Specifically describing, in the normal balanced walking, the PP value (PP1 to PP6) and the one step time T (T1 to T6) barely have a difference in the right foot step (odd number step) and the left foot step (even number step), as shown in FIG. 4(A) and FIG. 5(A). Therefore, the even number step PP value (PPodd)/odd number step PP value (PP even) and the one step time T of the even number step (Todd)/one step time T of the odd number step (Teven) becomes a value close to one (within reference range), and determination can be made that the balance is satisfactory.

On the other hand, if walking while nursing the left foot, the PP value (PP1 to PP6) and the one step time T (T1 to T6) have a large difference in the right foot step (odd number step) and the left foot step (even number step), as shown in FIG. 4(B). Therefore, the even number step PP value (PPodd)/odd number step PP value (PP even) or the one step time T of the even number step (Todd)/one step time T of the odd number step (Teven) becomes a value far from one (outside reference range), and determination can be made that the balance is unsatisfactory.

If walking while dragging the right foot, a bias occurs in the one step time and the amplitude for the left foot step and the right foot step as shown in FIG. 5(B). Therefore, the even number step PP value (PPodd)/odd number step PP value (PP even) or the one step time T of the even number step (Todd)/one step time T of the odd number step (Teven) becomes a value far from one (outside reference range), and determination can be made that the balance is unsatisfactory.

Figure 6:
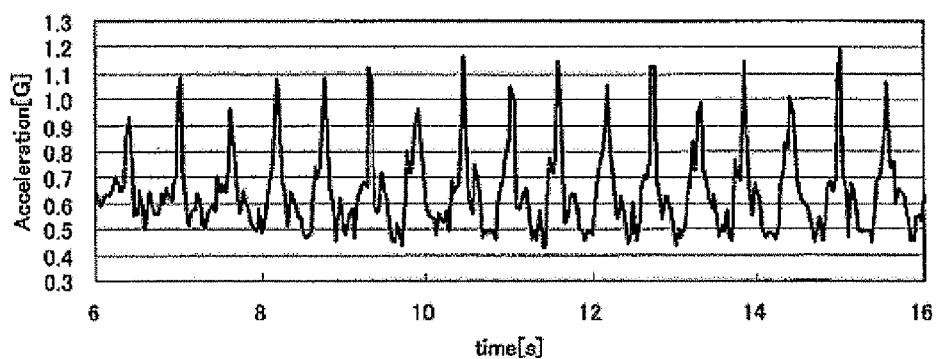
FIGS. 6(A) and 6(B) are views describing an output waveform of an acceleration detection unit at the time of walking when the upper half of the body is tilted.
Figure 6:
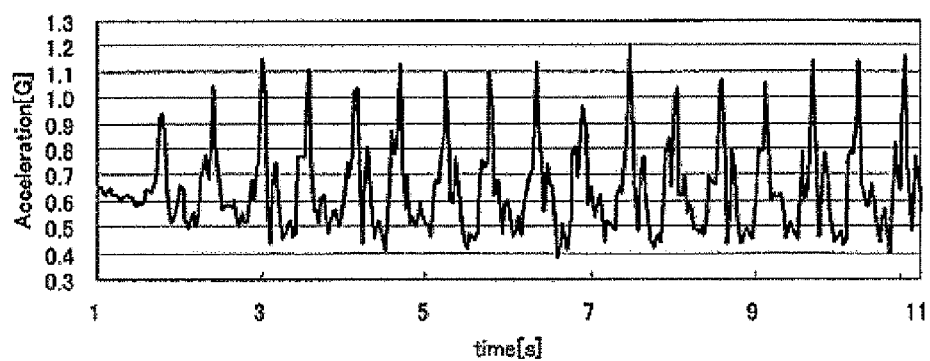

If the upper half of the body is tilted to the right as shown in FIG. 6(A) or the upper half of the body is tilted to the left as shown in FIG. 6(B), a bias occurs in the one step time and the amplitude for the left foot step and the right foot step. Therefore, the even number step PP value (PPodd)/odd number step PP value (PP even) or the one step time T of the even number step (Todd)/one step time T of the odd number step (Teven) becomes a value far from one (outside reference range), and determination can be made that the balance is unsatisfactory.

Therefore, an unsatisfactory balance can be detected in various walking balances, and a notification can be made to the user. Therefore, the body motion measurement device 1 for detecting the walking balance can be used for training to walk beautifully like a fashion model, used for training healthy walking with a satisfactory walking balance, and used for the progress management of rehabilitation for gait training.

Since the walking balance can be detected with only the body motion measurement device 1, the work of laying down pressure sensors on the floor is not necessary, and the body motion measurement device 1 with excellent convenience capable of detecting a walking balance in walking at various locations in the daily life can be provided.

Since the unsatisfactory walking balance can be notified to the user through various methods, the user can recognize the unsatisfactory walking balance and be conscious of walking with a satisfactory walking balance.

Since a value obtained by dividing one of the value of even number step (one step time or amplitude) and the value of odd number step (one step time or amplitude) with the other (i.e., not absolute value, but relative value of even number step and odd number step) is used, satisfactory and unsatisfactory in the walking balance can be determined irrespective of the individual difference such as the length of stride of each person and the magnitude of the up and down movement during walking.

In the correspondence of the configuration of the present invention and the embodiment described above, the body motion balance detection device and the computer of the present invention correspond to the body motion measurement device 1 of the embodiment; and similarly, the acceleration sensor corresponds to the acceleration detection unit 12, the body motion related signal and the acceleration signal correspond to the detection signal of the acceleration detection unit 12, the output means and the display means corresponds to the display unit 13, the body motion balance display corresponds to the notification and figure of balance abnormality displayed on the display unit 13, emission or flashing of LED, the audio guidance of an audio output device, or the vibration of a vibration device, the body motion balance detection means corresponds to the calculation unit 14 for executing step S9, step S13, or steps S9, S13, S16, the number of steps counting means corresponds to the calculation nit 14 for storing the counted number of steps after step S4, the number of steps display corresponds to the calculation unit 14 for displaying the counted number of steps after step S4, the storage means corresponds to the storage unit 16, the power supply means corresponds to the power supply unit 18, the foot information corresponds to PPodd, Todd, PPeven, and Teven, the amplitude of the acceleration signal corresponds to PPodd and PPeven, the one step time of the acceleration signal corresponds to Todd and Teven, the continuity determination process corresponds to step S7, the amplitude comparison process corresponds to step S8, the foot information acquiring process corresponds to step S8 and step S12, the body motion balance detection process corresponds to step S9, step S13, or steps S9, S13, S16, the one step time comparison process corresponds to step S13, the predetermined number of steps corresponds to ten steps, the criterion corresponds to first to fourth balance criterion values, the criterion specification accepting means corresponds to the operation unit 17, the acceleration signal in the vertical direction of an exercising living body corresponds to the vertical component of the acceleration signal, the acceleration signal in the horizontal direction of an exercising living body corresponds to the horizontal component of the acceleration signal, and the body motion balance corresponds to the bias in the one step time and the amplitude of the right foot and the left foot during walking, where the present invention is not limited only to the configuration of the above described embodiment, and various embodiments can be obtained.

For instance, the body motion measurement device 1 may be configured to detect not only the walking balance but the body motion balance such as walking balance, stepping balance or thigh up balance. In such a case, the body motion balance of the user wearing the device, the foot exercise balance related to the foot exercise (walking, running, stepping, thigh up) of the user wearing the device, or the left and right balance in the horizontal direction of the user wearing the device in various exercises can be detected.

The body motion measurement device 1 can be configured to more finely set the first to fourth balance criterion values to narrow the range for determining as normal or output the value of PPodd/PPeven or Todd/Teven as it is. Thus, the slight difference in the body motion balances can be detected, which becomes useful in the diagnosis of the body motion balance of an athlete and in the diagnosis for recovery of the exercise ability in rehabilitation. In such a case, the appropriate range (range in which the body motion balance is determined as satisfactory) can be narrowly set according to the improvement in the body motion balance if the first to fourth balance criterion values can be set in detail with the operation of the operation unit 17.

Figure 7:
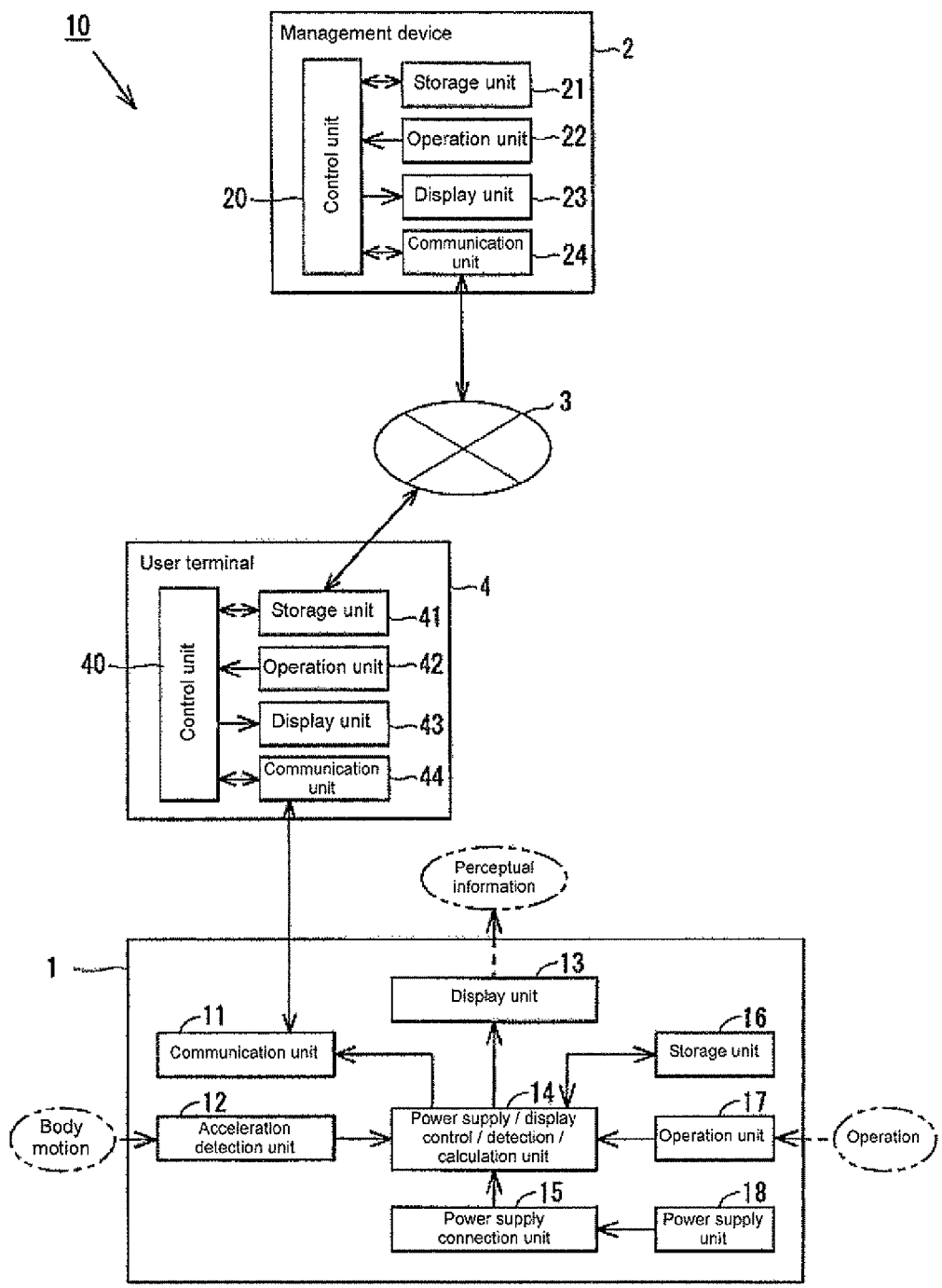
FIG. 7 is a configuration of a body motion balance detection system.

Furthermore, a user terminal 4 capable of communicating with the body motion measurement device 1 through the communication unit 11 and a management device 2 capable of communicating with the user terminal 4 through an Internet 3 may be arranged to obtain a body motion balance detection system 10, as shown in FIG. 7.

In this case, the management device 2 is, for instance, an appropriate computer used as a server device, and includes a control unit 20, a storage unit 21, an operation unit 22, a display unit 23, a communication unit 24, and the like. The communication unit 24 can be configured by an appropriate communication device such as a wire connected LAN board or a wireless LAN board for wireless communication.

The management device 2 receives data from the body motion measurement device 1 through the user terminal 4 by the operation of the operation unit 22 performed by an attendant, and displays an output screen based on such data on the display unit 23. The output screen displays the number of steps, the normal/abnormal of the balance, and the like.

The user terminal 4 is configured by, for instance, a personal computer and the like, and includes a control unit 40, a communication unit 41, an operation unit 42, a display unit 43, and a communication unit 44. The communication unit 41 can be configured by an appropriate communication device such as a wire connected LAN board or a wireless LAN board for wireless communication. The communication unit 44 can be configured by an appropriate communication interface such as a wire connected USB (Universal Serial Bus) or Bluetooth (registered trademark) for wireless communication.

The user terminal 4 has a function of acquiring data from the body motion measurement device 1 through the communication unit 44 and displaying graphs and tables based on the data on the display unit 43, and a function of transmitting the data to the management device 2. The number of steps, the normal/abnormal of the balance, and the like are displayed on the screen displayed on the display unit 43.

The user terminal 4 is not limited to a personal computer and may be configured by an appropriate device such as a portable information processing device including PDA (Personal Digital Assistants) or a portable telephone.

With such a configuration, instructors and doctors can confirm the body motion balance in real time and carry out coaching and diagnosis satisfactorily by displaying the detection results and the determination results of the body motion balance on the display means (display unit 43 and display unit 23) of the information processing terminal (user terminal 4 and management device 2). Furthermore, instructors and doctors can change the reference in real time by adopting the configuration of inputting the first to fourth criterion values with the operation means (operation unit 42 and operation unit 22) of the information processing terminal (user terminal 4 and management device 2). In this case, it can be configured such that the first to fourth balance criterion values and the body motion balance detection program may be stored in the information processing terminal (user terminal 4 and management device 2), and calculation may be performed by the information processing terminal (user terminal 4 and management device 2) when receiving the acceleration signal from the body motion measurement device 1.

The present invention may be used not only in a case like humans walking with two legs, but to detect the body motion balance of animals walking with four legs or walking with two legs such as pets and breeding animals. In this case, the present invention can be made in health checkup of pets and breeding animals that cannot talk about symptoms, such as diagnosing whether the pets or breeding animals are walking while nursing a leg.

INDUSTRIAL APPLICABILITY

The present invention can be used in the body motion balance detection device, the body motion measurement device, the body motion balance detection method, the body motion balance detection program, and the body motion balance diagnosis method for detecting the body motion balance.

Furthermore, the present invention can be used not only in a case like humans walking with two legs but to detect the body motion balance of animals walking with four legs or walking with two legs such as pets and breeding animals.

The invention claimed is:

1. A body motion balance detection device comprising:
a body motion related signal acquiring unit that acquires a body motion related signal in which a change in a body motion of a living body is detected, the body motion related signal acquiring unit acquiring the body motion related signal when the body motion related signal acquiring unit is attached to the living body;
a body motion balance detection unit that detects a body motion balance from the body motion related signal acquired by the body motion related signal acquiring unit; and
an output unit that performs an output based on the detected body motion balance, wherein
the body motion balance detection unit is configured to execute:
a foot information acquiring process for recognizing one step unit from the body motion related signal, and acquiring foot information on each respective foot of the living body, and
a body motion balance detection process for detecting the body motion balance based on the foot information, and
a detecting unit that determines whether the body motion related signal is indicative of walking, wherein
the detection of the body motion balance by the body motion balance detection unit is executed when walking is determined,
the foot information acquiring process acquires information of an odd number step and information of an even number step by separating the foot information of the odd number step and the even number step, and
the body motion balance detection process detects an abnormal balance of the body motion balance by comparing the information of the odd number step and the information of the even number step.

2. The body motion balance detection device according to claim 1, wherein
the body motion balance detection process compares an average value of information of the odd number step and an average number of information of the even number step.

3. The body motion balance detection device according to claim 2, wherein
the body motion balance detection unit is further configured to execute:
a continuity determination process for determining whether it is possible to continuously acquire information about the body motion for every step, and if continuously acquired, information from the body motion related signal becomes the foot information, and
the body motion balance detection unit executes the foot information acquiring process and the body motion balance detection process if the information is continuously acquired for a predetermined number of steps, and does not execute the detection of the body motion balance if the information is not continuously acquired for the predetermined number of steps.

4. The body motion balance detection device according to claim 1, wherein
the body motion balance detection process compares an average value of the information of the odd number step and an average value of the information of the even number step.

5. The body motion balance detection device according to claim 4, wherein
the body motion balance detection unit is further configured to execute:
a continuity determination process for determining if the body motion related signal acquiring unit can continuously acquire information about the body motion for every step, and if continuously acquired, the information from the body motion related signal becomes the foot information, and
the body motion balance detection unit executes the foot information acquiring process and the body motion balance detection process if the information is continuously acquired for a predetermined number of steps, and does not execute the detection of the body motion balance if the information is not continuously acquired for the predetermined number of steps.

6. A body motion measurement device comprising:
a portable body motion detection sensor that detects a change in body motion of a living body when the portable body motion detection sensor is attached to the living body;
a step counting unit that counts a number of steps from a body motion related signal detected by the portable body motion detection sensor;
a body motion balance detection unit that detects body motion balance from the body motion related signal detected by the portable body motion detection sensor;
a display unit that displays a number of steps of the counted number of steps counted by the step counting unit and the body motion balance detected by the body motion balance detection unit;
a storage unit that stores the counted number of steps; and
a power supply unit that supplies power, wherein
the body motion balance detection unit is configured to execute:
a foot information acquiring process for recognizing one step unit from the body motion related signal, and acquiring foot information on each respective foot of the living body, and
a body motion balance detection process for detecting the body motion balance based on the foot information, and
a detecting unit that determines whether the body motion related signal is indicative of walking, wherein
the detection of the body motion balance by the body motion balance detection unit is executed when walking is determined,
the foot information acquiring process acquires information of an odd number step and information of an even number step by separating the foot information of the odd number step and the even number step, and
the body motion balance detection process detects an abnormal balance of the body motion balance by comparing the information of the odd number step and the information of the even number step.

7. A body motion balance detection method comprising:
detecting a body motion balance from a body motion related signal by a body motion related signal acquiring unit in which a change in a body motion of a living body is detected, the body motion related signal acquiring unit acquiring the body motion related signal while attached to the living body; and
performing an output based on the detected body motion balance, wherein
the body motion balance detection step includes:
recognizing, by a foot information acquiring process, one step unit from the body motion related signal, and acquiring foot information on each respective foot of the living body, and
detecting, by a body motion balance detection process, the body motion balance based on the foot information,
determining, by a detecting unit, whether the body motion related signal is indicative of walking, the detection of the body motion balance by the body motion balance detection step is executed when walking is determined,
acquiring, by the foot information acquiring process, information of an odd number step information of an even number step by separating the foot information of the odd number step and the even number step, and
detecting, by the body motion balance detection process an abnormal balance of the body motion balance by comparing the information of the odd number step and the information of the even number step.

8. A non-transitory computer-readable storage medium that stores an executable program thereon, wherein the program instructs a microprocessor to perform the method of claim 7.

9. A body motion balance diagnosis method comprising:
attaching a body motion balance detection device on a median line of a living body, the body motion balance detection device including (1) a body motion related signal acquiring unit that acquires a body motion related signal in which a change in a body motion of the living body is detected; (2) a body motion balance detection unit that detects a body motion balance from the body motion related signal acquired by the body motion related signal acquiring unit; and (3) an output unit that performs an output based on the detected body motion balance, wherein
the body motion balance detection unit executes the steps of:
recognizing, by a foot information acquiring process, one step unit from the body motion related signal, and acquiring foot information on each respective foot of the living body, and
detecting, by a body motion balance detection process, the body motion balance based on the foot information,
determining, by a detecting unit, whether the body motion related signal is indicative of walking, wherein
the detection of the body motion balance by the body motion balance detection unit is executed when walking is determined;
making a diagnosis of the body motion balance according to the output based on the body motion balance from the output unit,
acquiring, by the foot information ac airing process, information of an odd number step and information of an even number step by separating the foot information of the odd number step and the even number step, and
detecting, by the body motion balance detection process, an abnormal balance of the body motion balance by comparing the information of the odd number step and the information of the even number step.

* * * * *